(12) United States Patent
Cichocki, Jr.

(10) Patent No.: US 8,257,393 B2
(45) Date of Patent: *Sep. 4, 2012

(54) ACTIVE SUTURE FOR THE DELIVERY OF THERAPEUTIC FLUIDS

(75) Inventor: Frank Richard Cichocki, Jr., Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 2505 days.

This patent is subject to a terminal disclaimer.

(21) Appl. No.: 10/727,367

(22) Filed: Dec. 4, 2003

(65) Prior Publication Data

US 2005/0125034 A1    Jun. 9, 2005

(51) Int. Cl.
    *A61B 17/04* (2006.01)
(52) U.S. Cl. .......... 606/228; 606/230; 604/46
(58) Field of Classification Search .......... 606/228–231; 604/890.1, 140, 93.01, 264, 272–274, 411, 604/4; 424/443; 57/237, 243, 220
See application file for complete search history.

(56) References Cited

U.S. PATENT DOCUMENTS

| 3,212,502 | A |   | 10/1965 | Myers |
|---|---|---|---|---|
| 3,474,703 | A | * | 10/1969 | Davis et al. ............. 87/1 |
| 3,821,956 | A |   | 7/1974 | Gordhamer |
| 3,918,455 | A |   | 11/1975 | Coplan |
| 4,159,720 | A |   | 7/1979 | Burton |
| 4,232,673 | A |   | 11/1980 | Bucalo |
| 4,650,473 | A |   | 3/1987 | Bartholomew |
| 4,673,565 | A |   | 6/1987 | Di Luccio et al. |
| 4,712,553 | A |   | 12/1987 | MacGregor |
| 4,880,002 | A |   | 11/1989 | MacGregor |
| 5,100,379 | A |   | 3/1992 | Wendell |
| 5,458,582 | A |   | 10/1995 | Nakao |
| 5,538,735 | A |   | 7/1996 | Ahn |
| 5,735,829 | A |   | 4/1998 | Cherian |
| 5,797,886 | A |   | 8/1998 | Roth et al. |

(Continued)

FOREIGN PATENT DOCUMENTS

FR    2747908 A    10/1997

(Continued)

OTHER PUBLICATIONS

International Search Report dated Jun. 10, 2005 for corresponding Appln. No. PCT/US2004/040488.

*Primary Examiner* — Elizabeth Houston
*Assistant Examiner* — Anh Dang
(74) *Attorney, Agent, or Firm* — Roberts Mlotlkowski Safran & Cole, P.C.

(57) ABSTRACT

An active suture that can be used for both wound closure and the delivery of therapeutic fluids to the tissue surrounding a wound is disclosed. The active suture may include a connector designed to join a fluid source, such as a syringe or conventional IV delivery system, to an internal passageway that is embedded within a braided suture. The internal passageway may be comprised of a fine polymeric tube and is capable of conducting and emitting a fluid into at least a portion of the braided suture and surrounding tissue. The invention enables delivery of an efficacious volume of drug bearing solution on the order of milliliters per day, provides a high level of fluid delivery rate control enabling the physician to start or stop drug administration at his/her discretion, and offers a means of providing more than one type of medication that may be selected post-surgically in accord with unexpected patient symptoms that may arise.

10 Claims, 11 Drawing Sheets

U.S. PATENT DOCUMENTS

| | | |
|---|---|---|
| 5,836,962 A | 11/1998 | Gianotti |
| 5,891,101 A | 4/1999 | Wilcox et al. |
| 5,914,973 A | 6/1999 | Jiang |
| 5,919,473 A | 7/1999 | Elkhoury |
| 5,984,933 A | 11/1999 | Yoon |
| 6,152,141 A | 11/2000 | Stevens et al. |
| 6,264,600 B1 | 7/2001 | Grimm |
| 6,350,253 B1 | 2/2002 | Deniega |
| 6,368,315 B1 | 4/2002 | Gillis et al. |
| 6,520,949 B2 | 2/2003 | St. Germain |
| 6,565,534 B1 | 5/2003 | Winters |
| 6,626,885 B2 | 9/2003 | Massengale |
| 7,875,055 B2 * | 1/2011 | Cichocki, Jr. ............ 606/228 |
| 2002/0029066 A1 * | 3/2002 | Foerster ............ 606/228 |
| 2002/0095133 A1 | 7/2002 | Gillis et al. |
| 2003/0028204 A1 | 2/2003 | Li et al. |
| 2005/0038472 A1 * | 2/2005 | Furst ............ 606/228 |
| 2005/0125034 A1 | 6/2005 | Cichocki, Jr. |
| 2006/0030883 A1 | 2/2006 | Cichocki, Jr. |

FOREIGN PATENT DOCUMENTS

| | | |
|---|---|---|
| GB | 1528955 A | 10/1978 |
| WO | WO 01/05210 A2 | 1/2001 |
| WO | WO 01/05210 A3 | 1/2001 |
| WO | WO 03/017854 A1 | 3/2003 |

* cited by examiner

ACTIVE SUTURE FOR THE DELIVERY OF THERAPEUTIC FLUIDS

FIELD OF INVENTION

The present invention relates to multifunctional devices that may be used to close surgical wounds. More particularly the invention relates to functional sutures that may be used to emit therapeutic or bioactive fluids to the tissue surrounding the suture while holding the wound closed. In particular, the invention relates to a braided suture having an internal passageway capable of conducting a fluid along at least a portion of the length of the suture that may be attached on one end, through a connector, to a fluid reservoir.

BACKGROUND OF THE INVENTION

Much benefit could be realized by delivering therapeutic fluids to the direct vicinity of the surgical wound. Reduced pain, enhanced wound healing, and reduced occurrence of surgical site infections are but a few potential benefits. However, the form and function of a device that could cost-effectively facilitate localized delivery of therapeutic fluids directly to the wound site over an extended period of time are not apparent. Intravenous (IV) delivery of medication to the patient following a surgical procedure is common practice. The physician may use an IV to deliver a wide variety of medications directly to the patient's blood stream over an extended period of time. Intravenous (IV) administration of medication is indeed a systemic method of drug delivery where the medication will circulate through the entire body before a portion of the medication is delivered to the wound site. Since much of the medication may be metabolized at other locations within the body before reaching the wound site, it is often necessary to increase the overall amount or concentration of medication to be delivered systemically with an IV in order for an efficacious amount to reach the wound site. However, in many cases, the increased concentration of medication that may provide the most efficacious result at the wound site, may not be safely delivered through an IV since toxic side effects may occur at various organs within the body. Other medications, such as certain local anesthetics, only provide an efficacious result when delivered locally and are simply not compatible with IV delivery methods.

Multiple injections in and around, before, during and after surgical procedures have been used in an effort to deter side effects and complications associated with surgical procedures. Although the syringe and hypodermic needle provide a means for localized drug delivery, the continuous delivery of medication via injection over an extended time period is not practical. Indeed, over time the medication dissipates to a concentration below that required to achieve a therapeutic effect and additional injections must be prescribed. Moreover, in the case where the surgical wound is the local target for drug treatment, multiple injections around the wound site may be required to achieve the desired therapeutic effect. The patient may suffer discomfort and repetitive disturbance if multiple injections must be repeatedly administered. As a further draw back, with this approach, the health care professional must dedicate their valuable time and attention to repeatedly apply localized injections.

In order to address the aforementioned shortcomings of the IV and injections for the localized and continuous delivery of therapeutic fluids, a number of specialized catheters have been developed. These specialized catheters typically exhibit multiple perforations along their lengths and are connected to a reservoir and pump that contain and feed the therapeutic liquid to the catheter, as described in U.S. Pat. No. 5,458,582, U.S. Pat. No. 5,891,101, and U.S. Pat. No. 6,626,885. The catheter itself may be placed directly into the surgical incision and held in place by closing the wound around it. Alternatively, the catheter may be driven through the tissue in the vicinity of the wound, leaving the tip of the catheter within the surgical wound and the body of the catheter firmly anchored in tissue surrounding the wound. Although these catheters provide a means of continuously delivering a drug to the wound, a number of drawbacks exists. The procedure can be invasive, since the catheter must typically be removed from the site of the wound before the patient can be discharged from the hospital. Some devices such as described in U.S. Pat. No. 6,626,885 require additional puncture wounds in the vicinity of the surgical wound to firmly secure the catheter in place, while others described in U.S. Pat. No. 5,891,101 and U.S. Pat. No. 5,458,582 require the use of additional sutures or a modification of the suturing procedure. Alternatively, in order to reduce patient discomfort and other complications associated with catheter removal, some catheter devices such as described in U.S. Pat. No. 5,458,582 may be produced from bioabsorbable materials. However, the implantation of bioabsorbable catheters increases the amount of material that must be absorbed and metabolized by the body, and it is generally desirable to keep this bioburden to a minimum. Finally, there are significant additional costs, ranging from tens to thousands of dollars, associated with the use of these specialized catheters and the supporting reservoirs and pumps that must be employed for their operation.

A suture that could be used for both wound closure and comprehensive localized drug delivery could satisfy the unmet needs of the aforementioned devices. The suture is implanted into the tissue surrounding the wound, which is indeed the region that may benefit most from localized drug delivery. Further, since the suture must be present in most cases to achieve wound closure, the number of invasive procedures that a patient must suffer is not necessarily increased. Likewise, there is no additional burden placed on the body to absorb a separate localized drug delivery device. Finally, the need to purchase specialized catheters and their supporting pumps and equipment may also be eliminated. Although a number of benefits may be achieved if comprehensive drug delivery from a suture were possible, the form and function of such a device is not apparent.

The concept of hollow monofilament sutures was first disclosed in U.S. Pat. No. 3,918,455. Although this patent focused on the use of hollow sutures to facilitate attachment to the suture needle, it was also suggested that the bore of the hollow suture could be filled with a fluid at the time of its installation to expedite dissolution of the suture material or render the suture visible by X-radiography. It was further suggested that the tube could be so extruded and drawn to be converted into a microporous state. In this state, the polymer comprising the wall of the hollow suture would permit fluid contained in the bore of the suture to gradually diffuse through the wall into the surrounding tissue. In U.S. Pat. No. 5,984,933 an apparatus for suturing tissue has been described. Although the patent focuses on a method and device to facilitate endoscopic suturing, it was suggested that the suture material of the device could be solid or hollow, and when the suture material is hollow, small holes in the wall of the suture can be formed to enable medicaments contained in the bore of the suture to leach out into the surrounding tissue. Although these patents suggest that hollow sutures may be used to contain, and in some embodiments even slowly emit a therapeutic fluid, there are some critical shortcomings that remain unaddressed. First of all, monofilament sutures are flaw sensitive. The introduction of pores or perforations into the wall of the hollow suture may result in a substantial decrease in the strength performance of the suture and lead to its inability to insure secure closure of the wound. Secondly, the amount of medicine that may be contained inside of a hollow suture is small. Indeed the maximum amount of drug bearing solution that may be contained within most hollow sutures is on the order of 0.005 ml or less, whereas many commercially available drug bearing solutions are efficacious only in quantities in excess of 1 ml. For example, anesthetic agents such as marcaine, lidocaine, bupivacaine, mepivacaine and procaine are typically injected into the tissue surrounding an incision or wound in a buffer solution at an overall volume ranging from 5 to 30 ml, which is 500 to 3000 times greater than the dose that is applicable with the hollow sutures disclosed in U.S. Pat. No. 3,918,455 and U.S. Pat. No. 5,984,933. Finally, once the hollow suture is implanted into the tissue surrounding the wound, the drug delivery rate is dictated by the rate at which the fluid leaches or diffuses through the multiple perforations or pores. Active control of the drug delivery rate is not possible. Furthermore, if an adverse reaction to the drug occurs, the suture must be excised from the wound to terminate drug delivery.

U.S. Pat. No. 4,159,720 describes a means for infusing liquids into tissue. The preferred embodiment comprises a reservoir for containing fluids attached outside the body that feeds liquid to an absorbent wick. The absorbent wick may be made from materials commonly used in the manufacture of sutures and may be installed in the tissue in a variety of ways including placement inside of the incision or deployment in the tissue surrounding the wound. The invention relies on capillary action to draw fluid in and control the delivery rate. As such, fluid delivery rate may not be increased or decreased at the physician's discretion. Moreover, the rate of fluid influx will depend on the type of wicking material used and the thickness and length of the wick installed. It is also important to note that in the cases when the suture is comprised of a material or is coated with a material that is not wetted by the fluid, wicking action will not occur and the device will not function. Even when the fluid to be delivered does indeed wet the wick, one may expect the fluid delivery rate driven by capillary forces that may be evolved within a suture to be several orders or magnitude slower than fluid delivery rates achievable by other means such as IV, catheter, or injection.

It is desirable to have of a suture that serves the multiple functions of wound closure and drug delivery. However, unlike the aforementioned examples of prior art, the suture should: 1) not compromise critical performance characteristics such as strength of the suture, 2) enable delivery of an efficacious volume of drug bearing solution on the order of milliliters not microliters, 3) provide a high level of drug delivery rate control and enable the physician to start or stop drug administration at his/her discretion, 4) provide a means of providing more than one type of medication that may be selected post-surgically in accord with unexpected patient symptoms that may arise, 5) function regardless of the composition of the suture material.

A suture that satisfies the aforementioned criteria for wound closure and drug delivery is disclosed herein. Components of the suture may include a connector designed to join a fluid reservoir, such as an IV or syringe, to a braided suture that contains at least one internal passageway capable of conducting a fluid along at least a portion of its length. The therapeutic fluid passes from the reservoir, through the connector, into the internal passageway and into the interstices between the multiple filaments of the braided suture. The integrity of the braided suture is not compromised in the design of this device and critical performance characteristic such as suture strength are maintained above United States Pharmacopia, USP, standards. By employing a connector to link the suture to an external reservoir, the amount of therapeutic fluid that may be delivered through the suture may be increased to a volume that is efficacious. Moreover, by regulating the supply of therapeutic fluid, the drug delivery rate may be actively controlled and more than one type of medication may be supplied as needed.

SUMMARY OF INVENTION

Described herein is an active suture comprising a braided suture having proximal and distal ends and an outer diameter; and at least one passageway coaxial with at least a portion of the braided suture, and having proximal and distal ends and a diameter that is less than the outer diameter of the braided suture; wherein the distal end of the at least one passageway is disposed between the proximal and distal ends of the braided suture.

Also described is an active suture comprising a braided suture having an outer diameter; and a tube coaxial with at least a portion of the braided suture, having an outer diameter that is less than the outer diameter of the braided suture and an inner diameter, and having one or more opening therein; wherein the ratio of the outer diameter of the tube to the inner diameter of the tube is greater than 1.7.

Further described is an active suture comprising a first braided suture having an outer diameter and having embedded therein a coated fiber tow or coated braided suture coaxial with at least a portion of the first braided suture, said coated fiber tow or coated braided suture having an outer diameter that is less than the outer diameter of the first braided suture, and said coated fiber tow or coated braided suture having one or more opening therein.

A method of administering a fluid to a wound is also described, where the wound has been closed using a braided suture having proximal and distal ends, an outer diameter, at least one passageway coaxial with at least a portion of the braided suture, said passageway having proximal and distal ends, an opening at the distal end and a diameter that is less than the outer diameter of the braided suture, wherein the distal end of the at least one passageway is disposed between the proximal and distal ends of the braided suture; and a connector attached to the proximal end of the at least one passageway; such that the distal end of the at least one passageway is at or in the proximity of the wound.

Further described herein is a method of closing a wound, optionally in combination with administering a fluid to a wound, using a suture/needle assembly comprising a braided suture having proximal and distal ends, an outer diameter, at least one passageway coaxial with at least a portion of the braided suture, said passageway having proximal and distal ends, an opening at the distal end and an outer diameter that is less than the outer diameter of the braided suture, wherein the distal end of the at least one passageway is disposed between the proximal and distal ends of the braided suture; a surgical needle attached to the distal end of the braided suture; and a connector attached to the proximal end of the at least one passageway.

DETAILED DESCRIPTION OF INVENTION

The invention disclosed herein is an active suture that may be used to close wounds while providing a means for delivering one or more therapeutic liquids to the direct vicinity of the wound, in a continuous or discontinuous fashion, over an extended period of time, without the need for additional invasive devices or procedures, without substantially increasing the amount of material that must be metabolized by the body, and without the need for investment in auxiliary devices or equipment.

Figure 1:
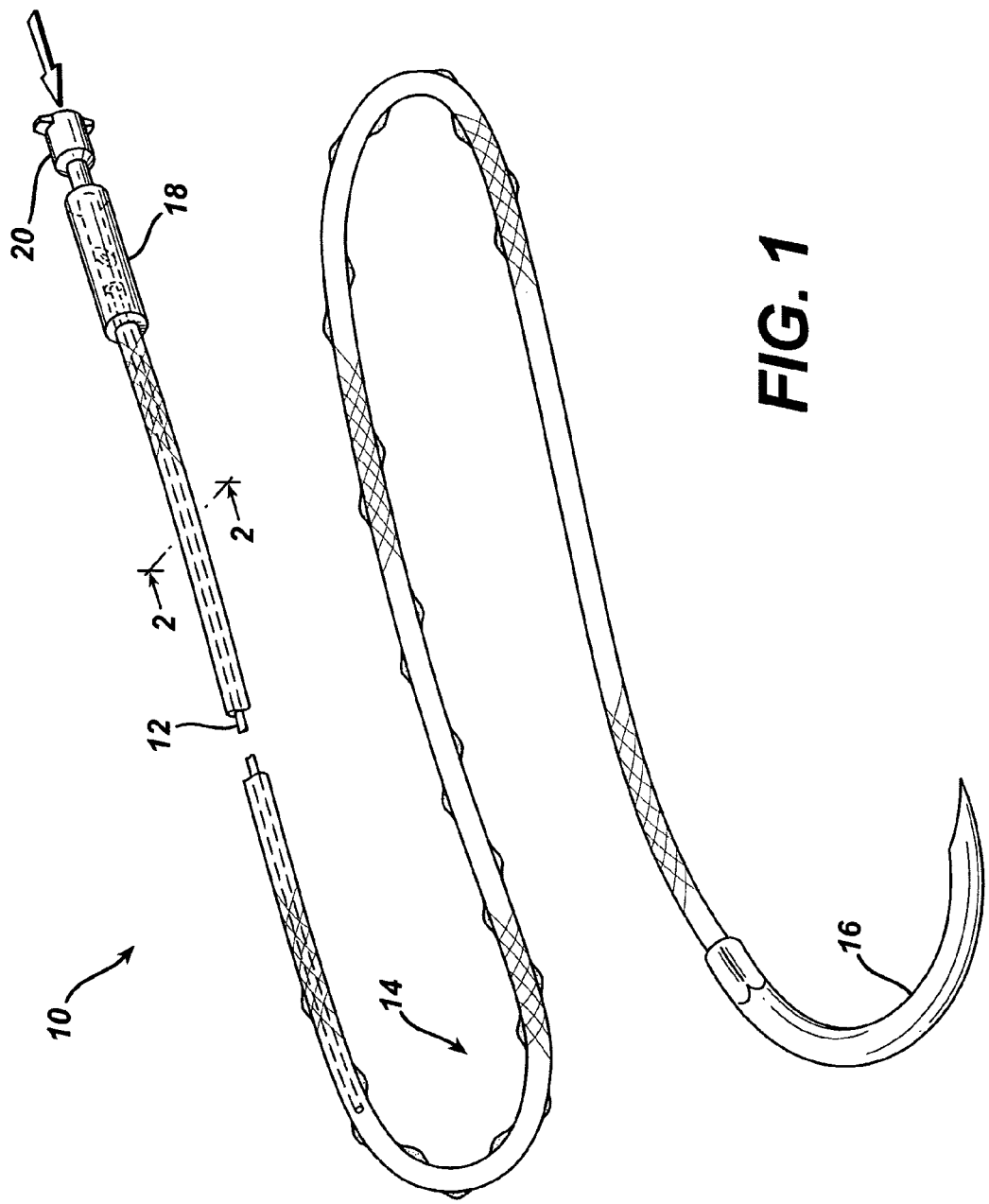
FIG. 1 is a schematic representation of an active suture.

The active suture 10, schematically depicted in FIG. 1, comprises a braided suture 14 with one or more internal passageway 12 capable of conducting and expelling a therapeutic fluid into at least a portion of the braided suture. The active suture may be connected to a suture needle 16 at the distal end and a connector 18 may be fitted to the proximal end of the active suture to enable fluid communication between an external fluid reservoir and the internal passageway 12 of the active suture. The connector 18 may be designed to directly accommodate a variety of conventional fluid reservoirs, including but not limited to a syringe 20, or indirectly via fittings that may in turn connect to conventional medical tubing attached to fluid pumps or intravenous (IV) delivery systems. Fluid may be delivered from an external fluid source, for example via pressure exerted on the fluid, through the connector and internal passageway and out the interstices of the braided suture to tissue surrounding the suture before, during, or after the wound closure procedure. The pressures exerted on or by the external fluid source may exceed any pressures that can evolve within the braided suture due to capillary or diffusional phenomena. Further, by controlling the pressures exerted on or by the external fluid source, the supply of fluid may be regulated and the fluid delivery rate may be actively controlled.

Figure 2:
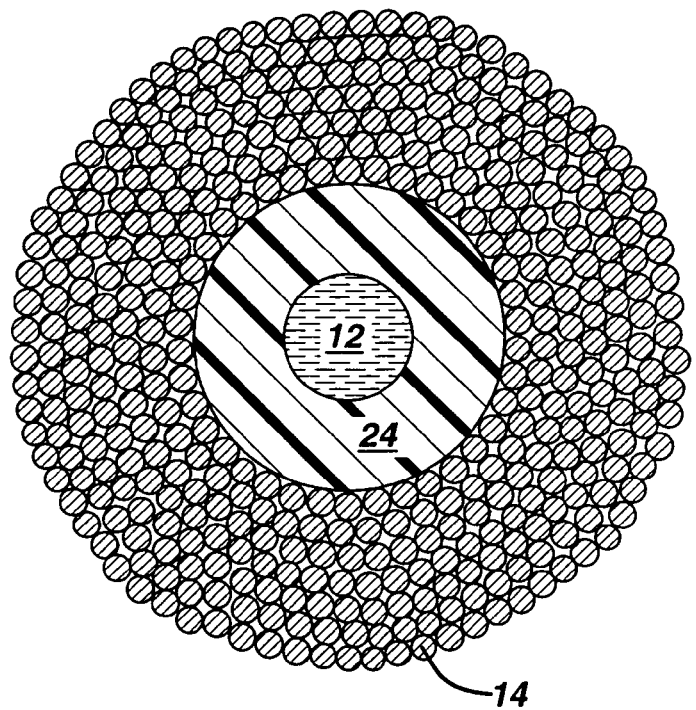
FIG. 2 is a schematic cross-sectional view along section A-A of FIG. 1 displaying a fine tube at the core.
Figure 3:
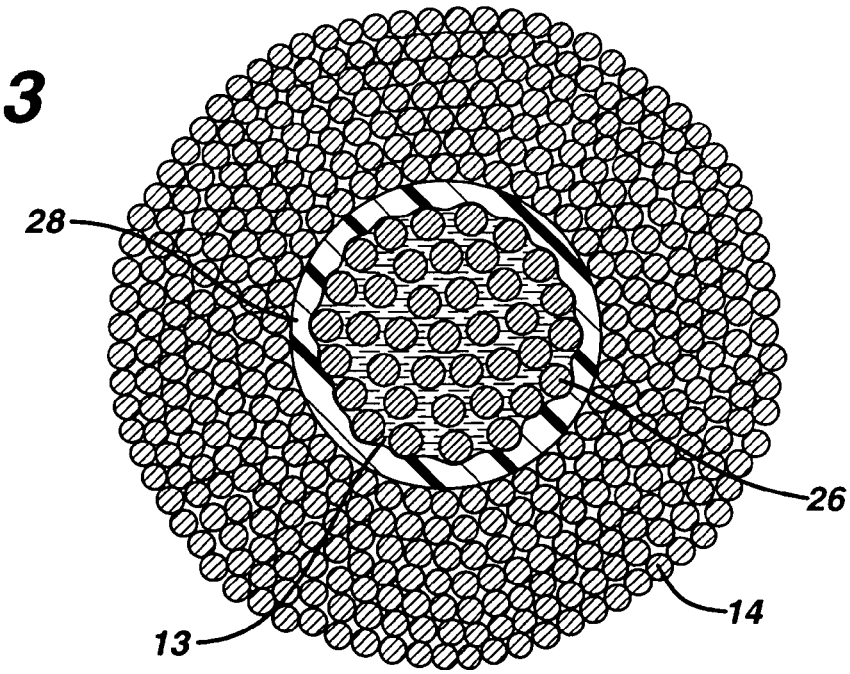
FIG. 3 is a schematic cross-sectional view along section A-A of FIG. 1 displaying a coated fiber tow at the core.

A critical component is the internal passageway for conducting fluid to the interstices of the braided suture. Transverse cross-sectional views of a braided suture taken along 2-2 of FIG. 1 that contain an internal passageway are schematically depicted in FIGS. 2 and 3. As shown in FIG. 2, the lumen 12 of a polymeric tube 24 that is woven into a braided suture 14 may serve as the internal passageway. Tubes used as the internal passageways that are incorporated into the braided sutures may take a variety of cross-sectional shapes including but not limited to circular, rectangular, and triangular. Likewise, the fluid conducting lumen may assume a variety of shapes including circular, trigonal, rectangular, as well as cross or star-shaped. Alternatively, as shown in FIG. 3, the interstices 13 between the multiple fibers or filaments of a fiber tow 26 or braided suture that has been coated with a polymer coating 28 may serve as the internal passageway.

Figure 4A:
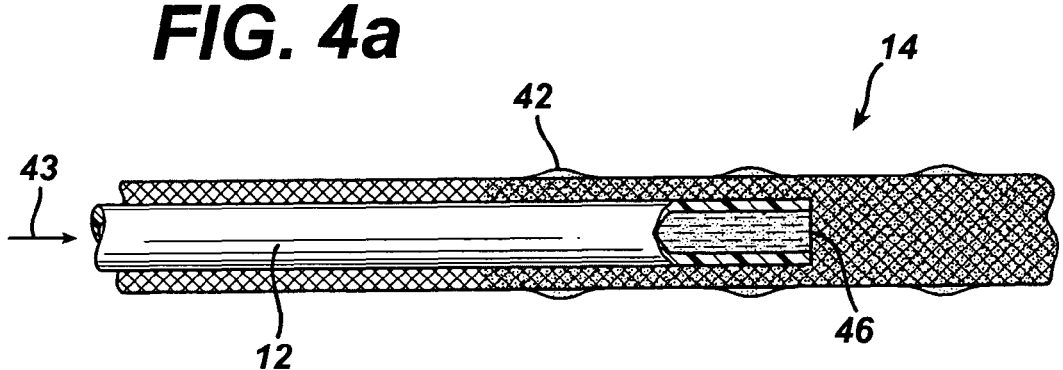
FIGS. 4a, 4b and 4c are cut away sections of the fluid emitting segments of the various embodiments of active sutures.

As depicted in the longitudinal cross-sectional view of a portion of an active suture shown in FIG. 4a, the internal passageway 12 may terminate within the braided suture 14 at a location between the connector and the suture needle. In this embodiment, fluid would enter through the connector 18 in FIG. 1, and travel within the proximal end of the active suture reaching location 43 of FIG. 4a, continuing on through the internal passageway 12, out the open end of the passageway 46, and into the interstices of the braided suture 14. The fluid accumulates within the interstices of the braided suture 14, eventually reaching the surface 42 where it may be dispensed into the surrounding tissue. In an alternate embodiment, the fluid may be emitted from several locations along the length of the internal passageway. As depicted in the longitudinal cross-sectional view shown in FIG. 4b, the internal passageway 12, receiving the fluid from location 43, may emit the fluid into the braided suture though one or more openings 48 along the length of the passageway as well as through the truncated end of the passageway 46. Openings in the passageway may be of practically any geometrical shape including, but not limited to circular, oval, and rectangular. Openings may also be of different sizes or be packed more densely at one location than another to achieve different rates of fluid delivery from different locations along the suture. Continuous openings in the passageway such as stripes or spirals may also be employed. In another embodiment, the internal passageway, containing at least one opening 48, may pass along the entire length of the active suture from the connector to the suture needle. As depicted in the longitudinal cross-sectional view of a segment of an active suture shown in FIG. 4c, fluid entering at location 43 may be emitted from one or more openings 48 along the length of the active suture. As with the embodiment depicted in FIG. 4b, the openings may assume a variety of geometrical shapes and may be distributed in variety of ways along the length of the suture.

Figure 4B:
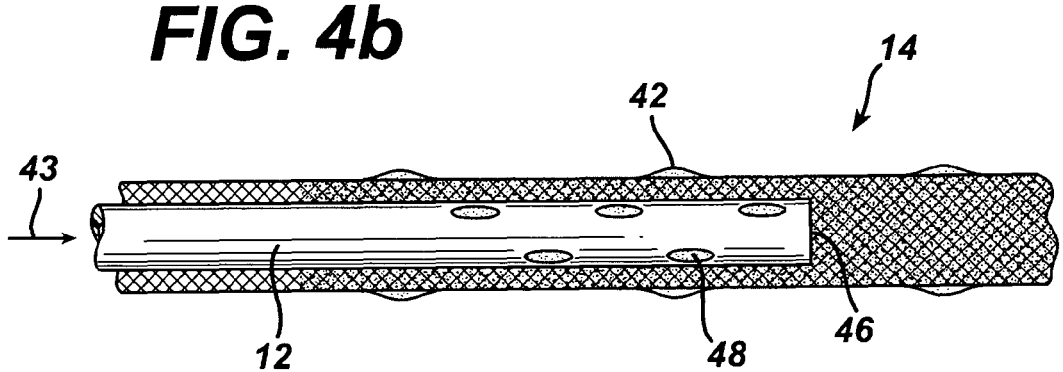
Figure 4C:
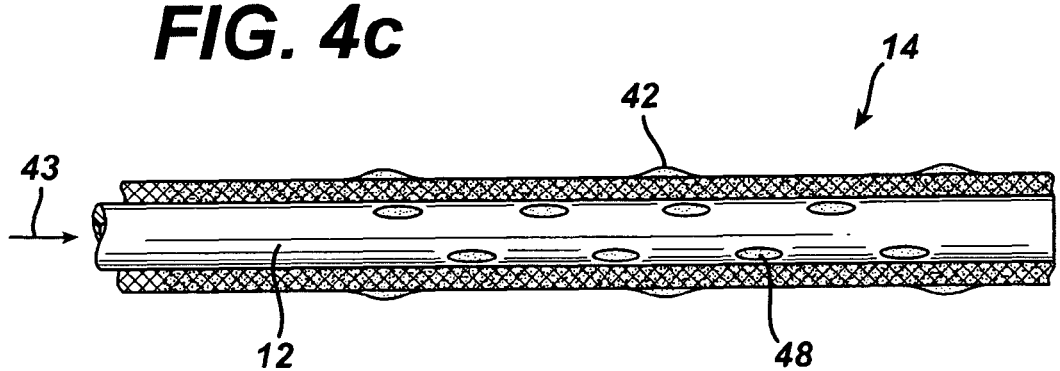
Figure 5:
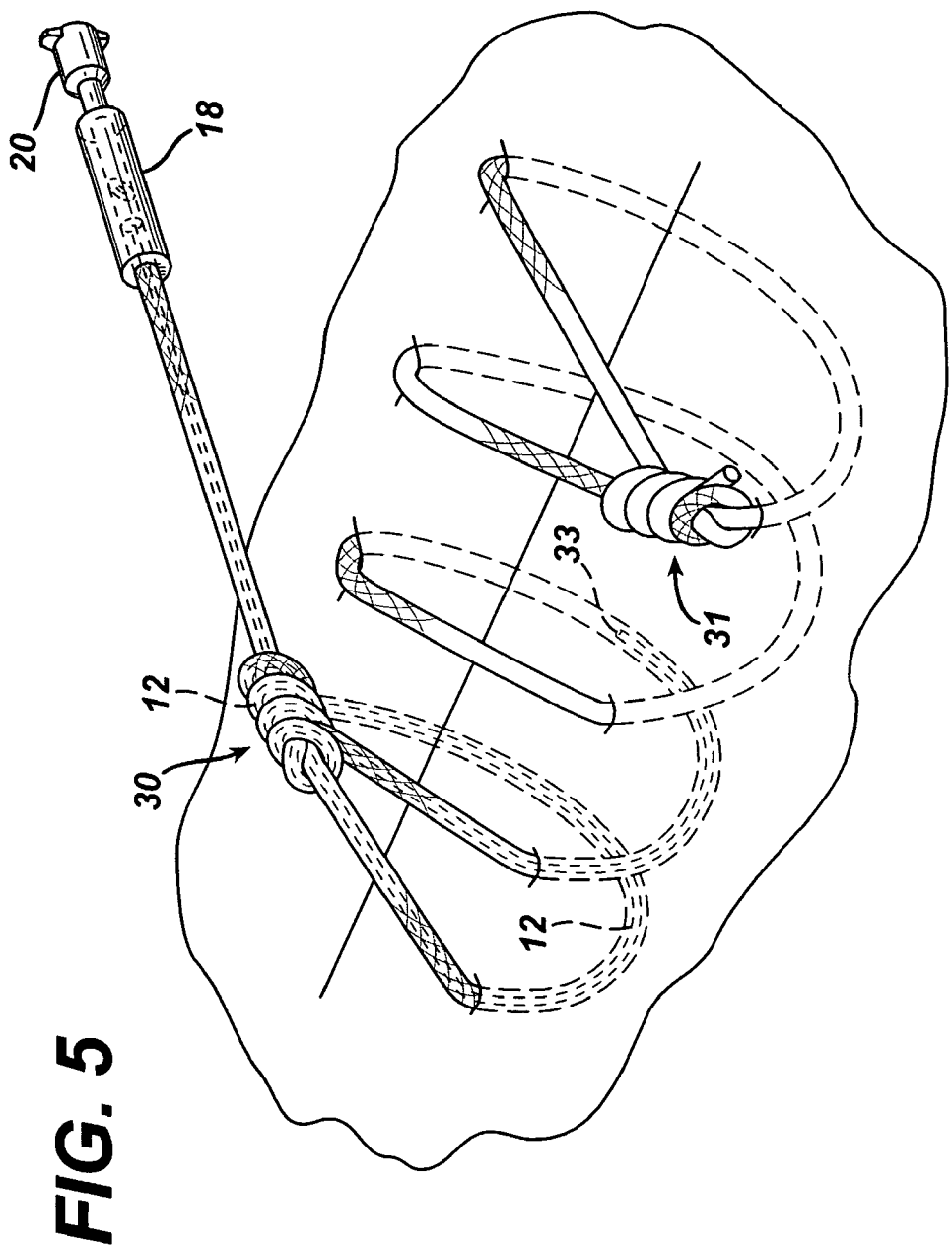
FIG. 5 is a schematic representation of an active suture that has been deployed using a continuous stitch.
Figure 6:
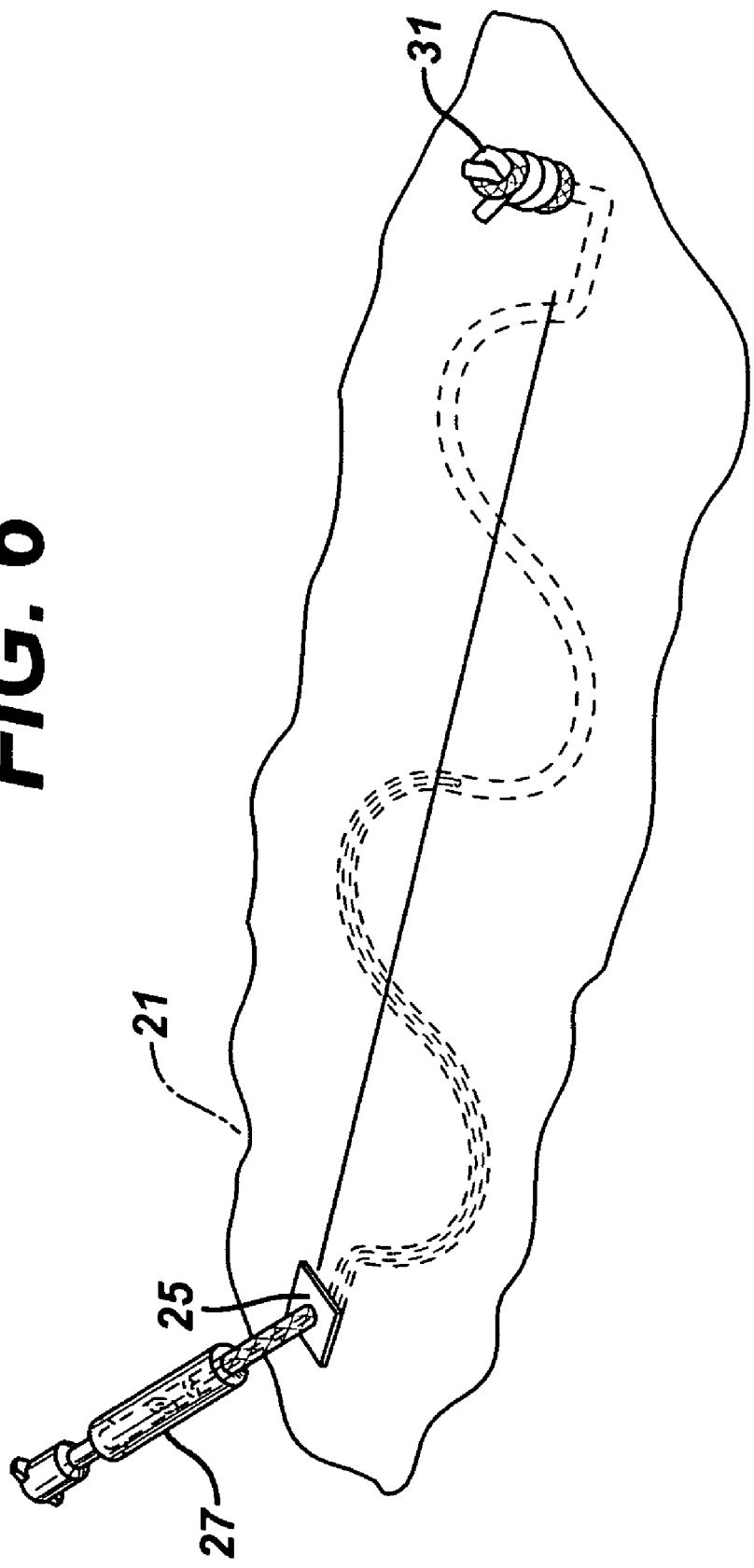
FIG. 6 is a schematic representation of an active suture that has been deployed using a continuous subcuticular stitch.

The active suture may be deployed to close a wound and deliver therapeutic fluids in a variety of ways. For applications involving post-operative drug delivery, both continuous and interrupted stitches may be used. A schematic depiction of a continuous stitch with an active suture is shown in FIG. 5. A first pass is made with the active suture and a series of anchoring knots 30 are tied. Alternately a suture anchor may be used in place of the knots to secure the proximal end of the suture. Subsequent passes through the tissue are made and a final series of knots 31 are tied to complete the suturing procedure. If the active suture is one of the embodiments shown in FIGS. 4a or 4b, the distal end of the internal passageway 33 and any openings in the internal passageway are preferably located between the first and last series of knots. If the active suture is the embodiment shown in FIG. 4c, the openings in the internal passageway are preferably located between the first and last series of knots. For the embodiment shown in FIG. 4a, for example, the therapeutic fluid would then be delivered from an external fluid reservoir 20 through the connector 18 and internal passageway 12 of the active suture, through the first series of knots 30 and into the braided suture 14 and tissue surrounding the wound. Other types of continuous stitches, such as the subcuticular stitch schematically represented in FIG. 6, may be employed as well. In this case, the active suture is driven through the skin 21 near one end of the incision. The active suture is then passed through the dermis below the epithelial layer using a serpentine pattern that spans the incision. At the opposite end of the incision a series of knots 31 may be tied to secure the stitch. It is important to note that with this embodiment a first series of knots to anchor the active suture in place is not absolutely necessary. Instead, a suture anchor 25 may be located between the connector 27 and the portion of the active suture that is embedded in the wound. Alternatively the connector may be designed to be substantially larger than the active suture diameter at its point of connection. With this approach, the active suture would be pulled though the first needle hole until the connector itself rested firmly against the tissue thereby serving as an anchoring device and eliminating the need to tie a first series of knots.

Figure 7:
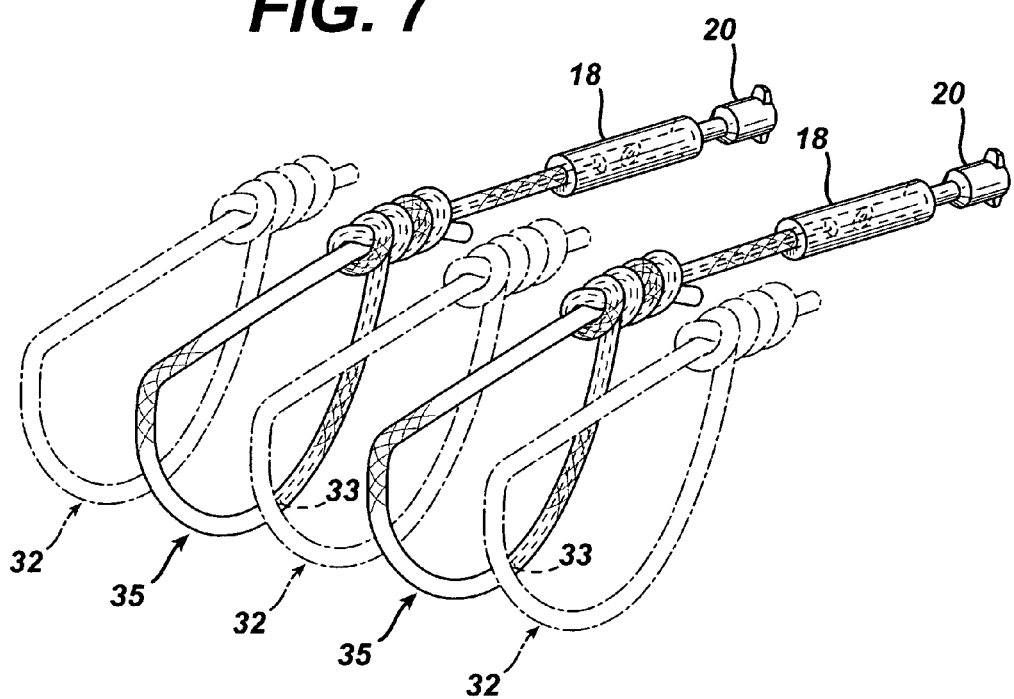
FIG. 7 is schematic representation of active sutures being deployed as interrupted stitches.

Alternatively, a series of interrupted stitches may be used to close the wound where one or more of the stitches is made with the active suture, as shown in FIG. 7. Standard, non-active sutures 32, may be used along side the active suture 35 to augment wound closure. As with the continuous stitch, the distal end of the internal passageway and any openings in the internal passageway of the embodiments shown in FIGS. 4a, 4b or 4c, for example, should lie in a portion of the active suture surrounding the wound. A therapeutic fluid may be delivered to the active sutures through the connector 18 from one or more independent sources 20.

Figure 8:
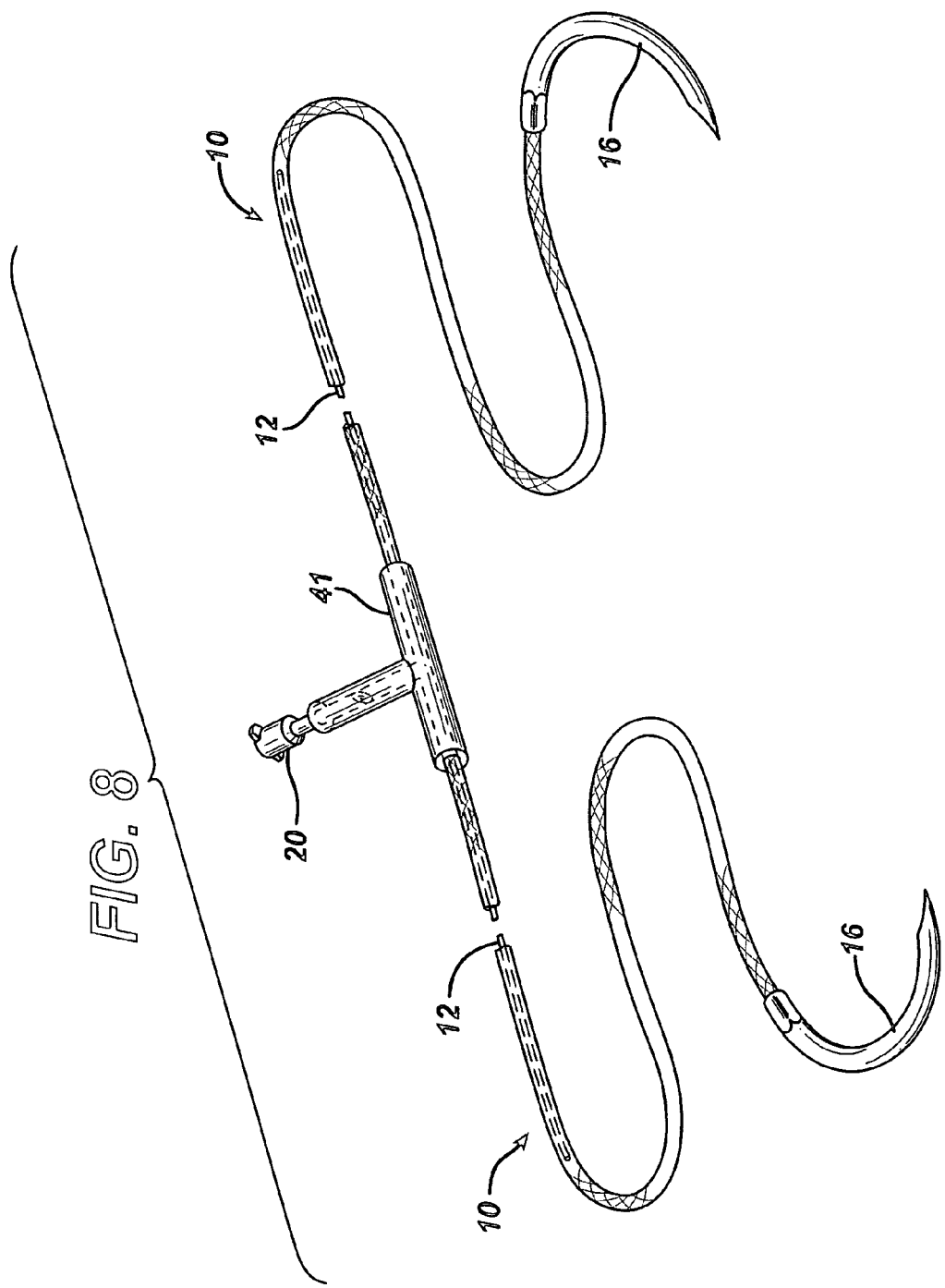
FIG. 8 is a schematic representation of the double-armed embodiment.
Figure 9:
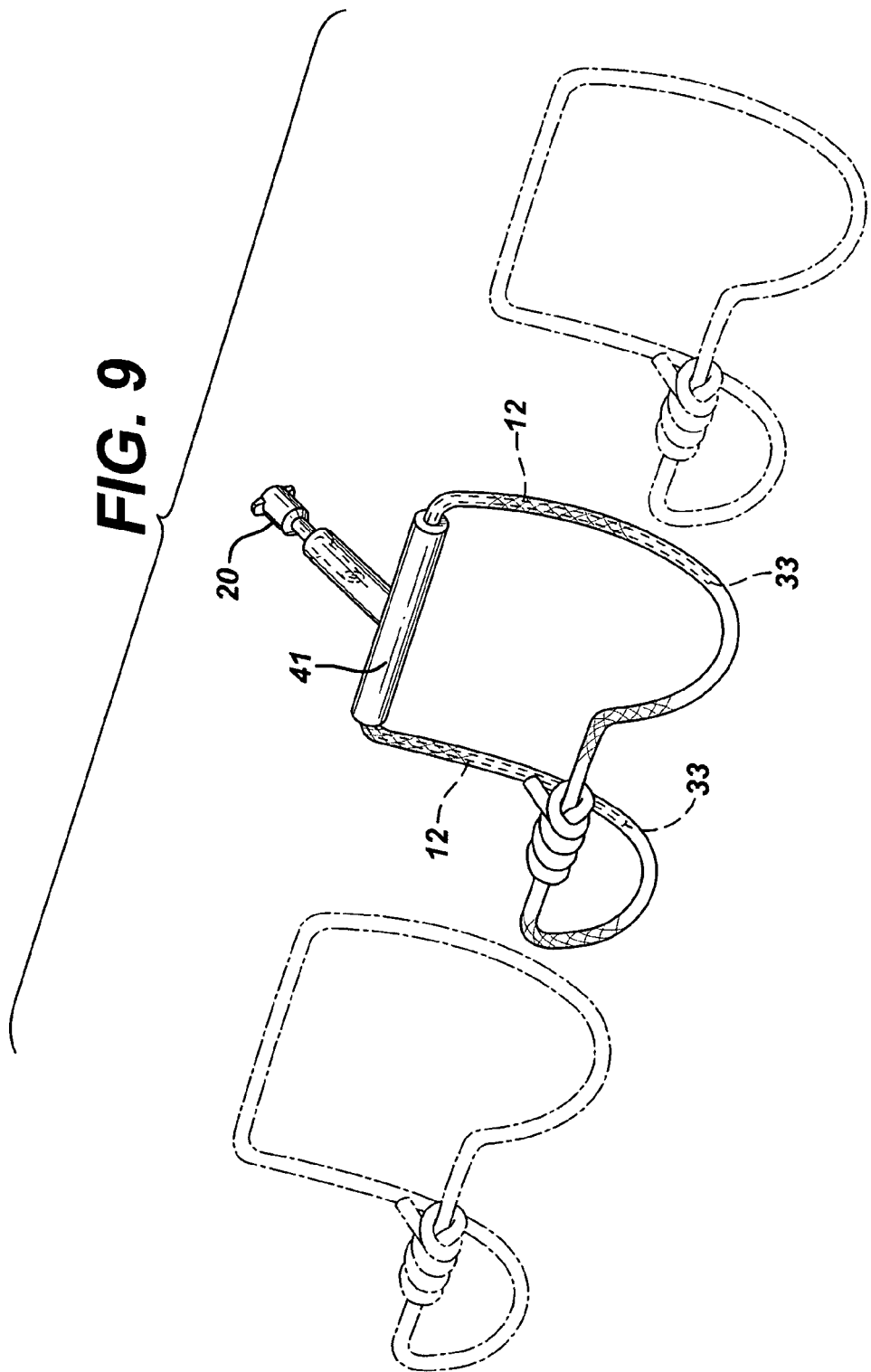
FIG. 9 is a schematic depiction of a method for deploying a double-armed active suture in an interrupted mattress stitch pattern.

The invention may also be embodied in the form of a double-armed suture, as schematically depicted in FIG. 8, wherein two suture needles 16 and a single connector are employed. In this embodiment, a connector 41 designed to receive fluid from an external fluid reservoir 20, is attached to the ends of the active sutures 10 in a manner that enables fluid communication with the internal passageways 12 of the active sutures. The double-armed suture may also be deployed in a variety of ways. A schematic representation of a double-armed suture 10 used with an interrupted horizontal mattress stitch is shown in FIG. 9. There are several advantages to using interrupted mattress stitches with the double-armed suture embodiment. As shown in FIG. 9, by allowing the connector 41 to serve as a portion of the active suture, it becomes unnecessary to tie knots in the portion of the active suture that contains the internal passageway 12. Additionally, since the internal passageway does not need to extend as far from the connector to effectively deliver fluid to the tissue, faster drug delivery rates may be achieved.

Figure 10:
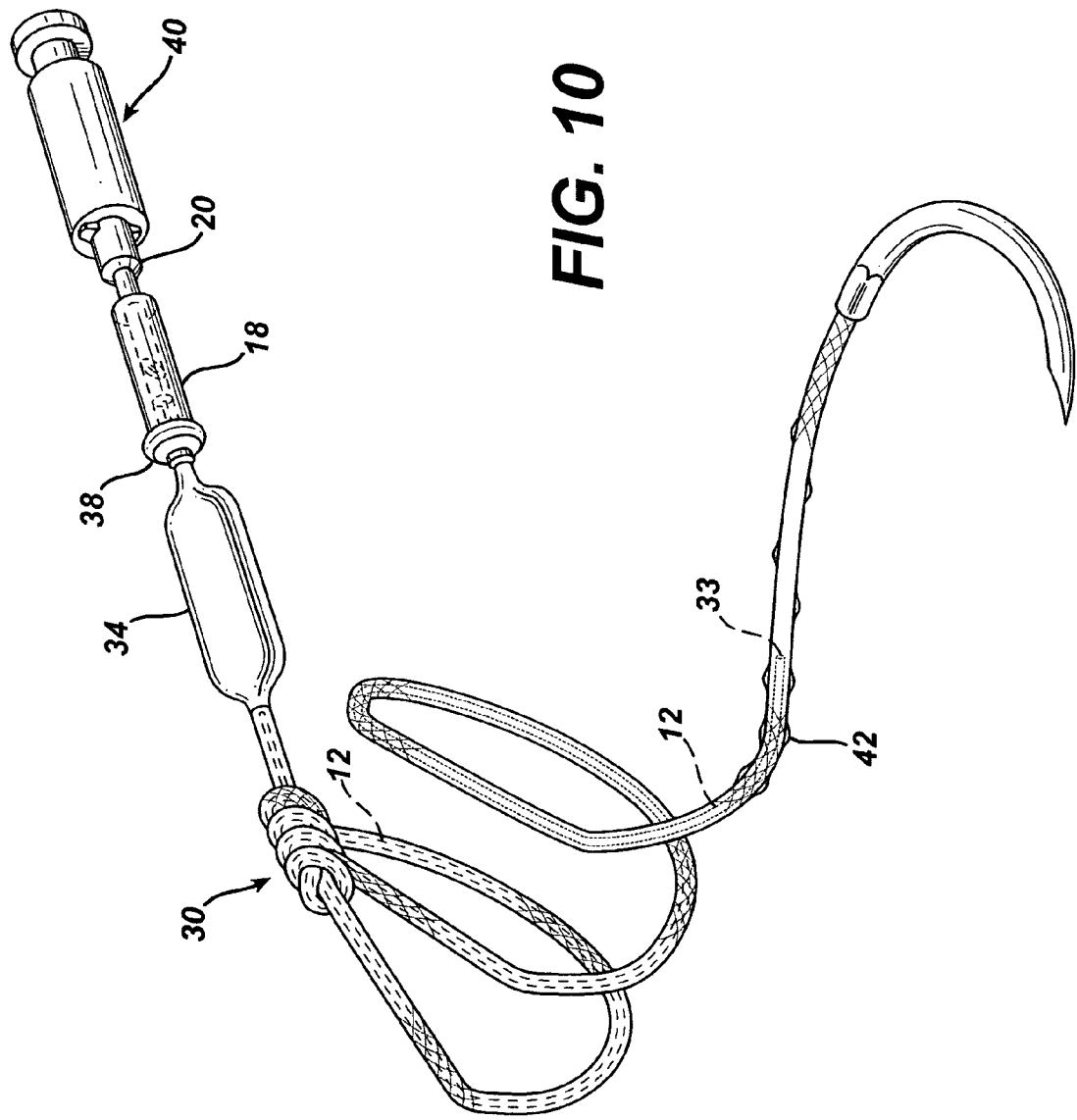
FIG. 10 is a schematic representation of an active suture being deployed perioperatively.

An alternate embodiment of the invention, shown in FIG. 10, employs an inflatable reservoir 34 produced from an elastomeric polymer that is attached in series between the proximal end of the internal passageway 12 of the active suture 10 and the connector 18. A syringe 40 may be attached to the connector 18 and used to inflate the reservoir. A clamp 38 may then be applied to a segment of the connector thereby collapsing and sealing the passageway of the connector. In an alternate embodiment, an elastomeric polymer may be used to occlude the passageway of the connector. The syringe needle 20 may then be used to puncture the elastomeric polymer in the passageway of the connector and the syringe would subsequently be depressed to inflate the elastomeric inflatable reservoir 34. Upon removal of the syringe from the connector, the elastomeric polymer contained within the passageway of the connector would shrink back to its original shape, closing the hole and forming a liquid tight seal. This embodiment may be used to deliver a therapeutic fluid to the tissue surrounding the wound both perioperatively and postoperatively. If used perioperatively, the opening(s) 33 in the internal passageway(s) 12 may occur anywhere along the length of the suture. If used post-operatively, at least one opening should exist in a segment of the suture that surrounds the wound.

The rate at which the fluid is emitted from the active suture is controlled predominantly be three factors: fluid viscosity, applied pressure, and passageway design. The Hagen-Poiseuille relationship for fluid flow through a cylindrical pipe may be used to approximate the volume flow rate of the fluid through the active suture with a passageway described by FIGS. 3 and 4a.

$$\text{Volume Flow Rate} = (\pi * \text{Applied Pressure} * \text{Radius}) / (8 * \text{fluid viscosity} * \text{Passageway length})$$

where, Applied Pressure is the pressure exerted by the fluid source, Radius is the effective radius of the internal passageway through which the fluid passes, and the Passageway length is the effective length of the internal passageway from the connector to the location of the opening in the passageway. If an IV is used, the applied pressure is determined by the height of the IV where $$\text{applied pressure} = \text{fluid density} * \text{gravitational constant} * \text{height of the IV above the patient.}$$

Figure 11:
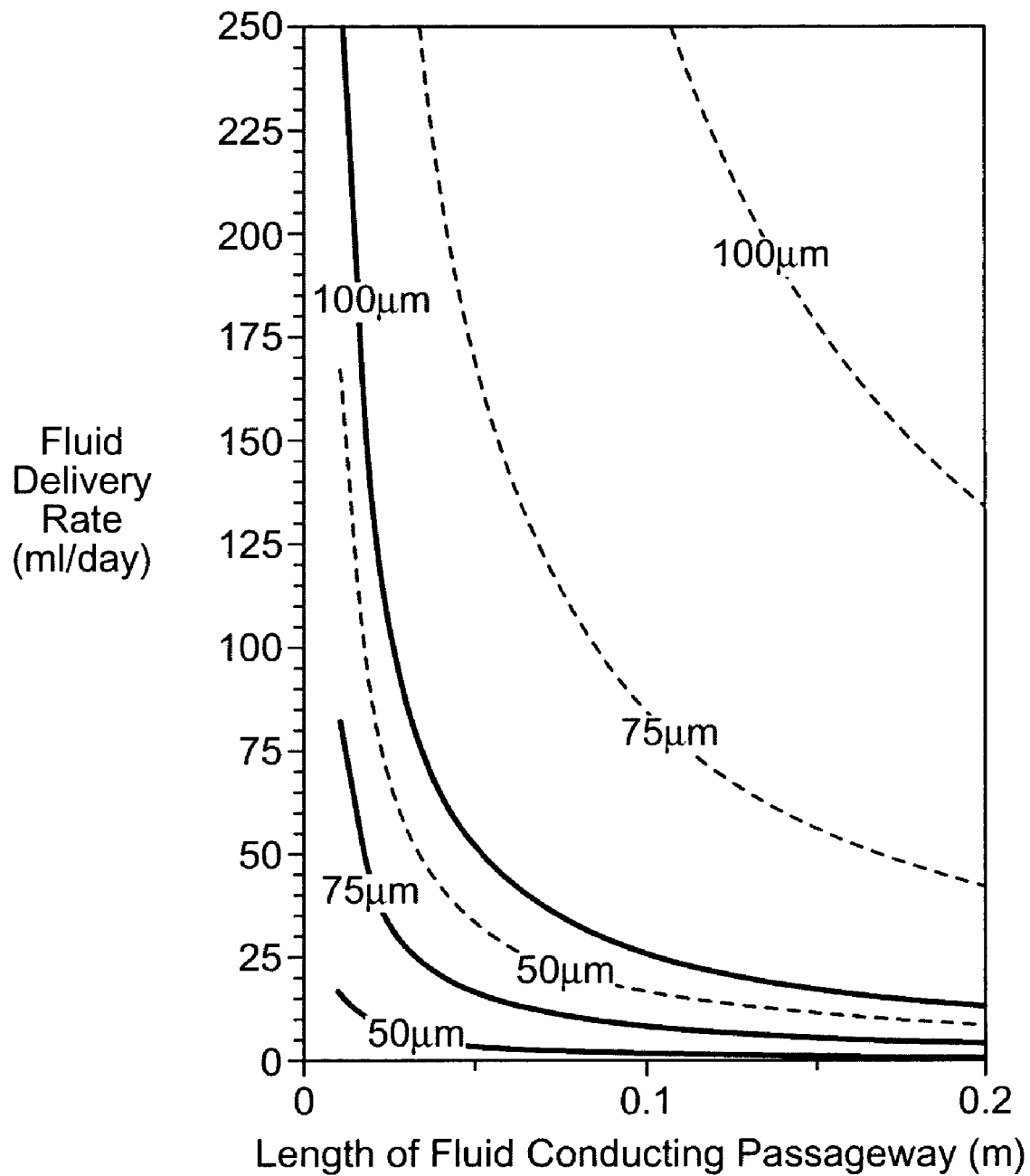
FIG. 11 is a graph of fluid delivery rate plotted against the length and diameter of the internal passageway.

For example if the IV bag is held approximately one meter above the wound site, approximately 0.1 atmosphere of applied pressure would drive the fluid through the active suture. If an elastomeric inflatable reservoir, similar to item 34 in FIG. 10 is used, the applied pressure that drives the fluid through the active suture may exceed one atmosphere. Finally fluid pumps, commonly used in conjunction with IV delivery systems, are tunable and may be used to deliver the fluid to the active suture at a variety of pressures and rates. In FIG. 11, the Hagen-Poiseuille relationship has been used to estimate the volume flow rate of water through active sutures that contain internal passageways, similar to the embodiment depicted in FIG. 4a, with lumens having inside diameters of 50, 75, and 100 μm that terminate within the braided suture at a distance of less than 0.2 m from the connector. The dashed curves of FIG. 11 represent the range of delivery rates attainable with one atmosphere of applied pressure. Elastomeric inflatable reservoirs, similar to those described in FIG. 10, can supply pressures on the order of one atmosphere. The solid lines of FIG. 11 represent the range of delivery rates attainable with approximately 0.1 atm of applied pressure. The fluid from an IV system with the IV bag held at a height of approximately 1 m above the wound site can generate this pressure. Both lumen diameter and length of the internal passageway strongly influence the rate of fluid flow, with smaller diameter lumens and longer passageways resulting in reduced delivery rates. It is important to note that FIG. 11 provides an estimate of drug delivery rate in the absence of knots. Knotting of the suture produces a more tortuous path for the internal passageway and can lead to slower delivery rates.

In many applications, it will be desirable to tie knots in the active suture to anchor it in position. In order for the active suture to conduct fluid, the lumen of the internal passageways must remain intact. If coated fiber tows or coated braided sutures are employed as the fluid conducting elements of the active sutures, as schematically depicted in FIG. 3, the fibers or filaments will support one another preventing excessive distortion and collapse of the internal passageways. However, if tubes are used to form the internal passageway, collapse and closure of the lumen can occur upon knot tying. In order to prevent closure of the lumens, tubes with sufficiently thick walls must be employed. Variables that influence the likelihood of collapse of the lumen inside of knots include thickness of the braided suture in which the internal passageway is imbedded, the stiffness of the tube, strength of the tube, and the overall tension applied in forming the knots. For active sutures that will be tied into surgically acceptable knots such as square knots or surgeons knots, preferably the ratio of the tube outside diameter (O.D.) to inside diameter (I.D.) is greater than 1.7 and more preferably, the ratio of the O.D. to I.D. is greater than 2.0 for most polymeric materials that are currently employed in sutures.

The active suture may be manufactured, for example, via steps that include: production of the fluid conducting element to be used as the internal passageway of the active suture, incorporation of the fluid conducting element into a braided suture to form the active suture, attachment of the proximal end of the active suture to a connector, and attachment of the distal end of the active suture to a suture needle. Fine tubes compatible in size and form with the active suture shown in FIG. 2, for example, may be produced using conventional polymer extrusion technology. The tubes may be extruded directly to the proper size or may be extruded to a larger than preferred size and subsequently reduced in size with conventional fiber drawing techniques. If coated fiber tows or coated braided sutures are selected to serve as the fluid conducting element of the active suture, as depicted in FIG. 3, the first step in production would involve a polymer fiber coating process. A polymer extruder may be outfitted with a die that allows a fiber tow or braided suture to pass through and as the tow or braided suture pass through the die, they become encapsulated with a polymer film. This process is similar to the wire-coating process used to coat metal wires with insulative polymers and is well-know in the art. The tubes, coated fiber tows or coated braided sutures may be subsequently processed to form holes or openings as shown in FIGS. 4b and 4c. These openings in the fluid conducting element may be formed with mechanical methods or may be produced with precision laser equipment. It is important to note that in several embodiments, the step of forming a series of openings along the length of the fluid conducting element is optional. Indeed, the embodiment depicted in FIG. 4a simply allows the fluid to emit through the end of the truncated passageway and does not call for openings to be formed along the length of the fluid conducting element. Once the tube, coated fiber tow or coated braided suture has been formed, it may be braided along with other fiber strands to form the active suture of FIGS. 4a, 4b or 4c. This is most easily accomplished by passing the tube, coated fiber tow or coated braided suture along side the core filaments of a braided suture thereby allowing the woven filaments of the braided suture to encircle the tube, coated fiber tow or coated braided suture. Alternate braiding schemes wherein the tube, coated fiber tow or coated braided suture is woven around the core filaments of the braided suture may also be envisioned. After braiding, the embodiments represented in FIGS. 4a and 4b may be produced by removing a portion of the tube or coated fiber tow or coated braided suture. This may be accomplished by grasping the tube, coated fiber tow or coated braided suture with precision needle holders and pulling it through the braided suture until only a portion of the tube, coated fiber tow or coated braided suture remains inside the braided suture to form the active suture. The excess material is then trimmed away and the ends of the active suture are either hot-tipped or tipped with an adhesive, as is common practice in the art of suture making, to prepare them for attachment to the connector and suture needle. The connector, generally in the form of a tube, with an inside diameter nominally equivalent to the outside diameter of the tipped active suture on one end and of the form that would accommodate a hypodermic needle or connect to tubing on the other, or in the form of a polymeric twist cap that fits onto a syringe or tubing from an IV system is fit over the active suture and sealed with either an adhesive or thermal bonding process.

Components of the active suture may be made from both bioabsorbable and non-absorbable materials. The sutures, tubes, coated fiber tows, coated braided sutures and connectors of this invention may be made from polymers that are commonly employed in the manufacture of sutures including but not limited to polypropylene, polyamides, polyethyleneterephthalate (PET), polytetraflouroethylene (PTFE), silk, polycaprolactone, polydioxanone, polyglycolide, polylactide, or blends of polycaprolactone, polydioxanone, polyglycolide or polylactide. Additionally, since the connectors do not necessarily become implanted in the body of the patient, they may be produced from even a broader variety of engineering polymers, including but not limited to polyvinyl chloride, polyurethane, polyesters, polyolefins and polyamides.

Fluids that may be utilized with any of the sutures described above include any therapeutic or bioactive agent or fluid, including but not limited to antimicrobial or antibiodic agents such as 2,4,4'-trichloro-2'hydroxydiphenyl ether, benzalkonium chloride, silver sulfadiazine, povidone iodine, triclosan, gentamiacin; anti-inflammatory agents, steroidal or non-steroidal, such as celecoxib, rofecoxib, aspirin, salicylic acid, acetominophen, indomethicin, sulindac, tolmetin, ketorolac, mefanamic acid, ibuprofen, naproxen, phenylbutazone, sulfinpyrazone, apazone, piroxicam, anesthetic agents such as channel blocking agents, marcaine, lidocaine, bupivacaine, mepivacaine, procaine, chloroprocaine, ropivacaine, tetracaine, prilocaine, levobupivicaine, and combinations of local anesthetics with epinephrine, opioid analgesic agents such as morphine, fentanyl, codine anti-proliferatives such as rapamycin, growth factors such as PGDF, scar treatment agents such as hylauronic acid, angio-genesis promoting agents, pro-coagulation factors, anti-coagulation factors, chemotactic agents, agents to promote apoptosis, immunomodulators, mitogenic agents, diphenhydramine, chlorpheniramine, pyrilamine, promethazin, meclizine, terfenadine, astemizole, fexofenidine, loratidine, aurothioglucose, auranofin, Cortisol (hydrocortisone), cortisone, fludrocortisone, prednisone, prednisolone, 6α-methylprednisone, triamcinolone, betamethasone, and dexamethasone; hemostatic agents such as thrombin, tranexamic acid, epinephrine; as well as antithrombotic agents.

EXAMPLE 1

Figure 12A:
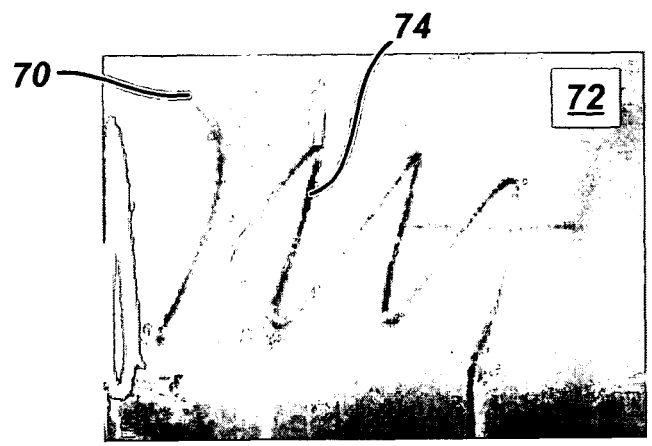
FIGS. 12a, 12b and 12c are a series of images that show the time-elapsed distribution of fluid from an active suture.
Figure 12B:
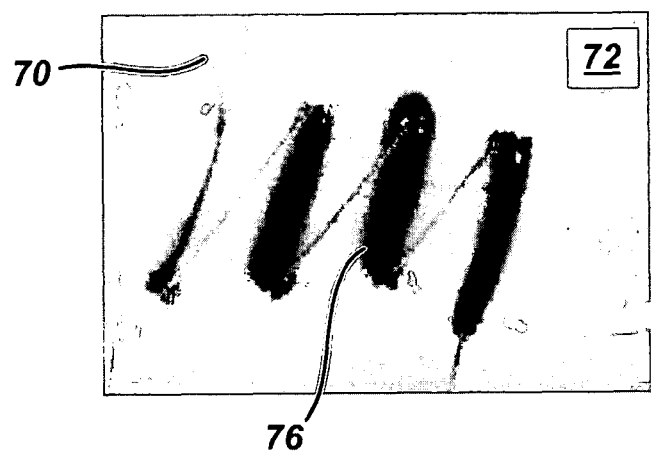
Figure 12C:
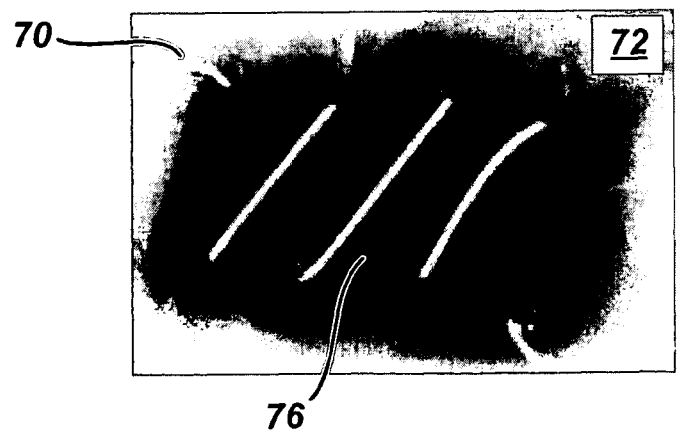

In order to demonstrate the ability of the active suture to distribute a fluid to surrounding tissue, a PET braided suture containing a polypropylene tube that terminates within the braided suture, as depicted in FIGS. 2, and 4a, was employed in an in vitro experiment wherein the active suture was passed multiple times though gelatin and subsequently connected to an IV delivery system that delivered water containing a blue pigment to the portion of the active suture that was imbedded in the gelatin. A series of time-elapsed images are shown in FIGS. 12a, 12b and 12c. FIG. 12a, taken at the onset of the experiment, shows the active suture 70 embedded in gelatin 72. The black mark on the active suture 74 indicates the location at which the internal passageway terminates. As time progresses, the pigment 76 spreads out around the active suture as shown in FIG. 12b. Ultimately, as shown in FIG. 12c, the fluid spreads to encompass the entire region surrounding the wound.

EXAMPLE 2

The incorporation of internal passageways into the active sutures should not compromise the tensile strength and knot tensile strength of the sutures to below standard acceptable levels. The knot tensile strengths of PET braided sutures in United States Pharmacopia (USP) standard sizes of 0 and 2 that have polypropylene tubes imbedded along side their core filaments were measured according to United States Pharmacopia (USP) standard 23. Size 0 sutures contained tubes with outside diameters of approximately 130 μm and inside diameters of ~75 um, and size 2 sutures contained tubes with outside diameters of approximately 230 um and inside diameters of ~135 um. For each test, at least 10 samples were tested per USP specifications. The performance of the PET braided sutures containing the polypropylene tubing at their core easily exceeded minimum performance requirements as set by USP standards, with average knot tensile strength values of 13.5 and 7.7 lbs for size 2 and 0 sutures respectively.

EXAMPLE 3

Experimental data indicates that extruded polymeric tubes produced from polypropylene, with outside diameters ranging from 0.005" to 0.010", with Youngs Moduli ranging between 0.1 and 3 GPa, with outside diameters (O.D.s) that are less than 1.7 times that of their inside diameters (I.D.s) will buckle and collapse when the braided sutures in which they are embedded are tied into square knots similar in form to those commonly used in surgical procedures. Similar experiments conducted with polymeric tubes comprised of polyethylene and polytetraflouroethylene with Youngs moduli ranging between 0.1 and 3 GPa with O.D. to I.D. ratios of greater than 2.3 do not collapse completely inside the square knots of the active suture and fluid can indeed be transferred through the knotted portions. For active sutures that will be tied into knots, preferably the ratio of the O.D. to I.D. is greater than 1.7. More preferably, the ratio of the O.D. to I.D. is greater than 2.0. In these experiments, the tubes were embedded in braided sutures produced from polyethyleneterephthalate (PET) fibers with USP sizes ranging from 2-0 to 5. Other variables that influence the likelihood of collapse of the lumen inside of knots include thickness of the braided suture in which the internal passageway is imbedded, strength of the fluid conducting tube, and the overall tension applied in forming the knots.

What is claimed:

1. An active suture comprising
   a braided suture having proximal and distal ends and an outer diameter, said braided suture having a plurality of interstices along at least a portion of its length; and
   at least one passageway coaxial with at least a portion of the braided suture, and having proximal and distal ends and a diameter that is less than the outer diameter of the braided suture and having one or more openings therein so that said at least one passageway conducts fluid to said plurality of interstices of said braided suture;
   wherein the distal end of the at least one passageway is disposed between the proximal and distal ends of the braided suture.

2. The active suture of claim 1, where the at least one passageway is a lumen of a tube.

3. The active suture of claim 2, where the tube has one or more holes that connect the lumen to the outer surface of the tube.

4. The active suture of claim 1, wherein said internal passageway comprises a polymer tube.

5. The active suture of claim 4, wherein the active suture can be tied into a surgeon's knot without collapse of the polymer tube at the location of said knot.

6. The active suture of claim 5, wherein the polymer is a bioabsorbable polymer.

7. The active suture of claim 5, wherein the polymer is a non-absorbable polymer.

8. The active suture of claim 7, wherein the polymer is polypropylene and the ratio of the outer diameter of the tube to the inner diameter of the tube is greater than 1.7.

9. The active suture of claim 7, wherein the polymer is polyethylene or polytetrafluoroethylene and the ratio of the outer diameter of the tube to the inner diameter of the tube is greater than 2.0.

10. The active suture of claim 1, wherein said internal passageway comprises a fiber tow coated with a polymer coating.

* * * * *